United States Patent [19]

Pocock

[11] 4,286,472
[45] Sep. 1, 1981

[54] FLEXIBLE FILTER

[75] Inventor: Robert E. Pocock, Highland Heights, Ohio

[73] Assignee: The Babcock & Wilcox Company, New Orleans, La.

[21] Appl. No.: 146,962

[22] Filed: May 5, 1980

[51] Int. Cl.$^3$ .............................................. G01N 1/22
[52] U.S. Cl. ................................ 73/863.24; 55/304; 422/101
[58] Field of Search .......................... 23/232 R, 230 A; 422/83, 101; 55/301, 302, 304, 379, 291, 505, 523; 73/23, 421.5 R, 421.5 A

[56] References Cited

U.S. PATENT DOCUMENTS

| 1,744,415 | 1/1930 | Pick | 422/83 |
| 3,722,186 | 3/1973 | Parker et al. | 55/505 X |
| 3,960,500 | 6/1976 | Ross et al. | 422/62 |
| 3,961,896 | 6/1976 | Dunn | 23/230 A X |
| 4,181,514 | 1/1980 | Lefkowitz et al. | 55/523 X |

FOREIGN PATENT DOCUMENTS 2810937  9/1979  Fed. Rep. of Germany ............. 55/523

*Primary Examiner*—Arnold Turk
*Attorney, Agent, or Firm*—James A. Hudak; Vytas R. Matas; Robert J. Edwards

[57] ABSTRACT

A filter assembly (10) adapted for use with a gas sample analyzing system. The filter is in the form of a flexible sleeve (20) formed from a heat resistant ceramic material which is received on an adapter (12) which fits over a probe (14) of the analyzing system. A V-shaped deflector plate (18) is attached to the adapter (12) beneath the filter and prevents the gas flow which is being sampled from impinging directly on the filter. The deflector plate (18) also sets up gas currents around the filter which cause the filter to flex or flutter, thus dislodging particulate material which tends to become trapped in the filter material.

7 Claims, 2 Drawing Figures

FLEXIBLE FILTER

TECHNICAL FIELD

The present invention relates generally to gas sampling analyzing systems, and more particularly to a filter for a sampling probe for such a system.

BACKGROUND ART

In systems for analyzing process gases and combustion flue gases, such as illustrated in U.S. Pat. No. 3,960,500, a sample probe extends into a gas duct to draw a gas sample into the analyzing system. To prevent particulate matter from being entrained by the probe and entering the analyzing system, the end of the probe is covered with a filter.

Prior art filters are generally made of a rigid material, and are thus susceptible to becoming clogged with particulate matter. While means can be provided to backflush the filter, if the particulate matter is sticky it cannot be easily dislodged by normal backflushing procedures.

Another problem associated with any form of filter which is subjected to process or combustion flue gases is that of high temperatures. Combustion gases can reach temperatures of 3000° F. or greater which greatly limits the materials which can be used for such a filter.

Because of this it has become desirable to develop a filter which minimizes the entrainment of particulate matter therein, can be backflushed to dislodge any particulate matter entrained therein, and which can be subjected to extremely high temperatures without any adverse effects.

SUMMARY OF THE INVENTION

The present invention solves the aforementioned problems associated with the prior art by providing a flexible filter that is formed from a temperature resistant fabric. This flexible filter fits over the end of the sample probe used in a gas sample analyzing system. An adapter fits over the other end of the sample probe and over the end of the probe support. The filter assembly includes a probe extension threaded into the adapter coaxial with the probe, a deflector plate welded or otherwise attached to the adapter and spaced from the probe extension toward the source of gas flow, and the flexible filter assembly enclosing the probe extension and attached to the adapter. The flexible filter assembly includes a coil spring received over the probe extension and a filter element in the form of an elongated closed-end sleeve or bag formed of a temperature resistant fabric, such as a continuous filament ceramic fiber, and received over the spring and secured to the probe extension. The deflector plate is substantially V-shaped in cross-section and is attached to the adapter with the legs of the V adjacent the filter assembly, and functions to prevent the gas flow from impinging directly on the filter element while insuring that there is sufficient gas movement along the sides of the filter to set up gas currents which cause the flexible filter element to deflect or flutter in the gas flow. This fluttering movement causes the fabric comprising the filter to flex which tends to dislodge particulate matter that becomes trapped in the fabric.

When the analyzer system is backflushed, the backflushing pressure causes the interstices within the fabric to open, thus dislodging any particulate matter which may not have been dislodged by the movement of the filter element during normal operation.

From the foregoing it will be seen that one object of the present invention is to provide a filter for a gas sample analyzer probe which will not tend to be clogged with particulate matter.

Another object of the present invention is to provide a filter which can withstand extremely high temperatures.

Yet another object of the present invention is to provide a filter which can be readily backflushed to insure complete cleaning.

These and other objects of the present invention will be more clearly understood after a review of the following description of the preferred embodiment of the invention when considered in conjunction with the following drawings.

DESCRIPTION OF THE PREFERRED EMBODIMENT

Figure 1:
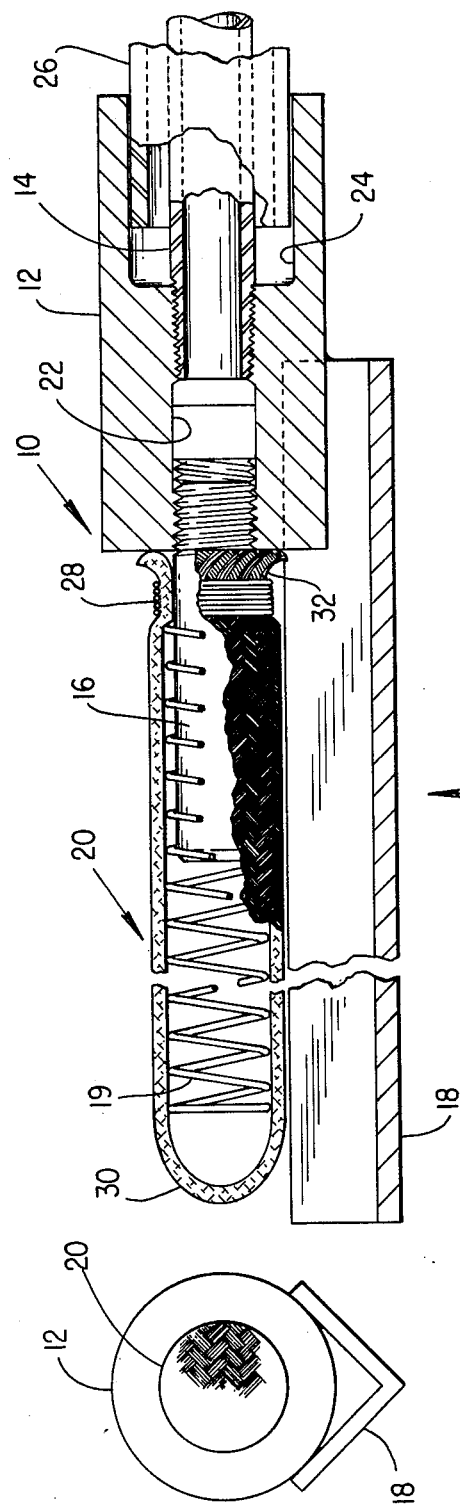
FIG. 1 is a longitudinal sectional view of the present invention with the components thereof shown in elevation.

Referring now to the drawings wherein the illustrations are for the purpose of describing the preferred embodiment of the invention and are not intended to limit the invention hereto. FIG. 1 shows a filter assembly 10 adapted for use with a gas sampling probe of the type illustrated in U.S. Pat. No. 3,960,500. The filter assembly 10 comprises a cylindrical adapter 12 which is threadably received on an analyzer probe 14 installed in a gas duct, a probe extension 16 threaded into the adapter 12, a deflector plate 18 attached to the adapter 12, a coil spring 19 received over the probe extension 16, and a filter element 20 received over the coil spring 19 and secured to the probe extension 16.

The cylindrical adapter 12 has a through bore 22 formed therein, and an enlarged counterbore 24 formed in one end thereof. The through bore 22 is threaded at one end to receive the probe extension 16, and is similarly threaded at the opposite end for attachment to the analyzer probe 14. The counterbore 24 is sized to provide clearance around a probe support member 26. The probe extension 16 is formed of a short length of pipe which is threaded at one end for engagement with the bore 22 of the adapter 12.

The coil spring 19 has one end thereof in an interference fit with the outwardly extending end of the probe extension 16, and the flexible filter element 20 is sized to be received over the spring 19. As shown in FIG. 1, the end of the filter element 20 can then be secured to the probe extension 16 by tightly wrapping it with heat resistant wire 28 or the like.

The filter element 20 is preferably in the form of a sleeve or bag having a closed end 30 and an open end 32 which is secured to the probe extension 16 by the wire 28. The filter element 20 can be formed of a continuous filament ceramic fiber woven into a braided sleeving. Such a fiber is capable of withstanding a continuous operating temperature of 2600° F., and intermittent temperature up to 3000° F. An example of such a fibrous material is 3M Brand AB 312 continuous filament ceramic fiber, which is composed of filaments of alumina-boria-silica having a density of 0.0975 lb/in$^3$, and an average denier (390 filament strand) of 900. The closed end 30 of filter element 20 can be formed by wrapping an open sleeve with heat resistant tape or wire, or the sleeve can be braided, woven or otherwise formed with one end closed, as illustrated in FIG. 1.

Figure 2:
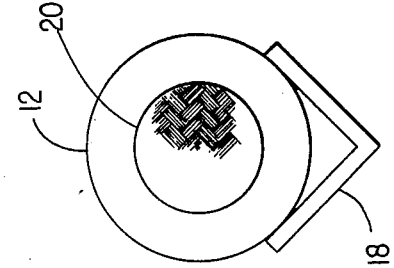
FIG. 2 is an end view of the invention illustrated in FIG. 1.

The deflector plate 18 can be a piece of metal formed in an angle or V in cross-section, as shown in FIG. 2, and welded to the cylindrical adapter 12. Th deflector plate 18 preferably extends at least as far outwardly from the end of the adapter 12 as the filter element 20 and prevents the gas flow, as represented by the arrows F, from impinging directly against the filter element 20.

In operation, the filter assembly 10 is threaded onto the end of the analyzer probe 14 installed in a gas duct, and is positioned so that the gas flow F strikes the apex of the V-shaped deflector plate 18 and flows around the flexible filter element 20. As the gas flows past the legs of the deflector plate 18 and along the filter element 20, currents are set up which cause the filter element 20 to deflect upwardly and downwardly so as to flutter causing the fabric which forms the filter to constantly flex as it filters out particulate matter from the gas being drawn in by the analyzer probe 14, thus dislodging particles which tend to be trapped within the fabric fibers.

When this analyzer system is backflushed by means of a fluid flowing outwardly through an analyzer probe 14, the fluid pressure which tends to build up within the filter element 20 causes the element to bulge which opens the interstices within the fabric to dislodge any particulate matter which may still be trapped in the filter element during normal operation of same.

Certain modifications and improvements will occur to those skilled in the art upon reading of the foregoing description. It should be understood that all such modifications and improvements have been deleted herein for the sake of conciseness and readability but are properly within the scope of the following claims.

I claim:

1. In a gas sampling system for analyzing gases within a duct, including a probe for withdrawing a sample of gas from the duct for analysis: a filter assembly attached to said probe and operable to filter the gas drawn into said probe, said filter assembly comprising a longitudinally extending flexible filter element formed of a temperature resistant ceramic material, support means for maintaining said longitudinal configuration of said filter element and a deflector plate substantially V-shaped and attached to said filter assembly to have the legs of the V of said deflector plate located adjacent the filter element of said filter assembly operable to shield said filter element from direct impingement of said gas flow and to provide sufficient gas flow along the sides of the filter element of said filter assembly to set up gas currents causing the filter element to flutter in the gas flow to dislodge any particulate matter trapped in the filter element.

2. The apparatus as defined in claim 1, wherein said filter assembly comprises an adapter member attached to said probe, a tubular extension attached to said adapter member and in combination with said probe, said filter element comprising a sleeve attached to said tubular extension.

3. The apparatus as defined in claim 2, wherein said support means includes a coil spring having one end in surrounding relation to said tubular extension, said sleeve being received over said coil spring.

4. The apparatus as defined in claim 2, wherein said filter element is formed of a fabric comprising alumina-boria-silica filaments.

5. The apparatus as defined in claim 4, wherein the length of said sleeve is substantially greater than its diameter, said sleeve being closed at one end and secured at its open end to said tubular extension by means wrapped around said sleeve adjacent said open end.

6. The apparatus as defined in claim 2, wherein said gas sampling system further includes a probe support in surrounding relation to said probe, said adapter member comprising a cylindrical member having a threaded bore formed therein for engagement with said probe, and a counterbore formed in one end thereof, said probe support being received within said counterbore.

7. The apparatus as defined in claim 6, wherein said tubular extension is received in said threaded bore.

* * * * *